United States Patent [19]

Casci et al.

[11] Patent Number: 4,741,891

[45] Date of Patent: * May 3, 1988

[54] SYNTHESIS OF ZEOLITE EU-2

[75] Inventors: John L. Casci, Redcar, England; Barrie M. Lowe, Edinburgh, Scotland; Thomas V. Lowe, Darlington, England

[73] Assignee: Imperial Chemical Industries PLC, London, England

[*] Notice: The portion of the term of this patent subsequent to Aug. 27, 2002 has been disclaimed.

[21] Appl. No.: 919,577

[22] Filed: Oct. 15, 1986

Related U.S. Application Data

[63] Continuation of Ser. No. 816,958, Jan. 6, 1986, abandoned, which is a continuation of Ser. No. 272,469, Jun. 11, 1981, abandoned.

[30] Foreign Application Priority Data

Jun. 12, 1980 [GB] United Kingdom .............. 8019211

[51] Int. Cl.$^4$ ........................................ C01B 35/10
[52] U.S. Cl. ........................... 423/277; 423/326; 423/328; 423/329; 423/330; 502/60; 502/77; 502/202
[58] Field of Search ........... 423/277, 326, 328, 328 C, 423/328 T, 329 T; 502/77, 202

[56] References Cited

U.S. PATENT DOCUMENTS

| | | | |
|---|---|---|---|
| 3,832,449 | 8/1974 | Rosinski et al. | 423/328 |
| 4,061,717 | 12/1977 | Kerr et al. | 423/329 |
| 4,104,294 | 8/1978 | Grose et al. | 260/448 C |
| 4,139,600 | 2/1979 | Rollmann et al. | 423/328 |
| 4,275,256 | 6/1981 | Chu et al. | 585/467 |
| 4,397,827 | 8/1983 | Chu | 423/326 |
| 4,423,021 | 12/1983 | Rollmann et al. | 423/326 |
| 4,456,582 | 6/1984 | Marosi et al. | 423/328 T |
| 4,495,166 | 1/1985 | Calvert et al. | 423/328 T |
| 4,537,754 | 8/1985 | Casci et al. | 423/277 |

FOREIGN PATENT DOCUMENTS

| | | | |
|---|---|---|---|
| 669 | 2/1979 | European Pat. Off. | |
| 0007081 | 1/1980 | European Pat. Off. | 423/328 |
| 0007098 | 1/1980 | European Pat. Off. | 423/328 T |
| 0015132 | 9/1980 | European Pat. Off. | 423/328 |
| 0042220 | 12/1981 | European Pat. Off. | 423/328 |
| 0046504 | 3/1982 | European Pat. Off. | 423/328 T |
| 0051318 | 5/1982 | European Pat. Off. | 423/328 |
| 0077523 | 4/1983 | European Pat. Off. | 423/328 T |

*Primary Examiner*—John Doll
*Assistant Examiner*—Jackson Leeds
*Attorney, Agent, or Firm*—Cushman, Darby & Cushman

[57] ABSTRACT

Zeolite EU-2 having a molar composition expressed by the formula:

0.5 to 1.5 $R_2O:Y_2O_3$: at least 70 $XO_2$:0 to 100 $H_2O$ wherein R is a monovalent cation or 1/n of a cation of valency n, X is silicon and/or germanium, Y is one or more of aluminium, iron, gallium or boron, and $H_2O$ is water of hydration additional to water notionally present when R is H, and having an X-ray pattern substantially as set out in Table 1 is prepared from a reaction mixture containing $XO_2$ (preferably silica), $Y_2O_3$ (preferably alumina) and a dicationic alkylated polymethylene diamine. The zeolite is useful in catalytic processes, especially for the conversion of methanol to hydrocarbons.

4 Claims, No Drawings

SYNTHESIS OF ZEOLITE EU-2

This is a continuation of application Ser. No. 816,958, filed Jan. 6, 1986, which is a continuation of application Ser. No. 272,469, filed June 11, 1981, both now abandoned.

The present invention relates to a novel zeolite material, hereinafter referred to as zeolite EU-2, to a method of making it and to processes using it as a catalyst.

According to the present invention we provide zeolite EU-2 having a molar composition expressed by the formula:

0.5 to $1.5R_2O:Y_2O_3$: at least $70XO_2:0$ to $100H_2O$ wherein R is a monovalent cation of 1/n of a cation of valency n, X is silicon and/or germanium, Y is one or more of aluminium, iron, gallium or boron, and $H_2O$ is water of hydration additional to water notionally present when R is H, and having an X-ray pattern substantially as set out in Table 1 (as determined by standard technique using copper K$\alpha$ radiation). Members of the EU-2 family of zeolites possess a unique crystalline structure whose X-ray diffraction pattern shows the significant lines listed in Table 1.

TABLE 1
Zeolite EU-2

| Interplanar Spacings d(A) | Relative Intensity 100 I/Io |
|---|---|
| 11.74 | 17 |
| 10.13 | 14 |
| 6.33 | 7 |
| 5.85 | 7 |
| 4.33 | 5 |
| 4.18 | 86 |
| 3.89 | 100 |
| 3.69 | 7 |
| 3.37 | 7 |
| 3.08 | 5 |
| 2.85 | 18 |
| 2.09 | 5 |

Within the above definition of chemical composition, the number of moles of $XO_2$ is typically in the range 100 to 5000 and zeolite EU-2 appears to be most readily formed in a state of high purity when the number of moles of $XO_2$ is in the range 150 to 3000.

This definition includes both freshly prepared zeolite EU-2 ("freshly prepared" means the product of synthesis and washing, with optional drying, as hereinafter described) and also forms of it resulting from dehydration, and/or calcination, and/or ion exchange. In freshly prepared zeolite EU-2, R may include an alkali metal cation; especially sodium, and/or ammonium, and usually or when prepared from alkylated nitrogen compounds, includes nitrogen-containing organic cations as described below or cationic degradation products thereof, or precursors thereof. These nitrogen containing cations are hereinafter referred to as Q.

The freshly prepared zeolite EU-2 may also contain nitrogen-containing compounds well in excess of the 1.5 moles set out in the aforesaid definition of the composition of zeolite EU-2, typically in the range 1 to 50 moles per mole of $Y_2O_3$. Since EU-2 is a zeolite, the excess base must be physically trapped within the crystal lattice, because it is too large to escape. It can be removed by thermal or oxidative degradation. This physically trapped basic material does not constitute part of the composition for the purposes of the definition. Thus a zeolite EU-2 as made typically has the following molar composition:

0 to $0.8M_2O:1.0$ to $50Q:Y_2O_3:100$ to $5000XO_2:0$ to $100H_2O$ wherein M is an alkali metal or ammonium, and $M_2O+Q \geqq 1.0$ The $H_2O$ content of freshly prepared zeolite EU-2 depends on the conditions in which it has been dried after synthesis.

In calcined forms of zeolite EU-2, R may be alkali metal but includes less or no nitrogen-containing organic compounds, since these are burnt out in the presence of air, leaving hydrogen as the other balancing cation.

Among the ion-exchanged forms of zeolite EU-2 the ammonium ($NH_4^+$) is of importance since it can be readily converted to the hydrogen form by calcination. The hydrogen form can also be prepared directly by exchange with an acid. The hydrogen-form and forms containing metals introduced by ion exchange are described further below.

Zeolite EU-2 is a novel zeolite with very characteristic molecular sieve properties as demonstrated by typical sorption results given in Table 2. These results pertain to sodium hydrogen EU-2 having a $SiO_2/Al_2O_3$ molar ratio of 450 (as described in Example 6).

TABLE 2

| | Sorption at 25° C. p/po = 0.5 | | | |
|---|---|---|---|---|
| Sorbate | Kinetic Diameter* $\sigma$A | Time (mins) | Wt sorbed g/100 g | Voidage available cc/100 g |
| Water | 2.7 | 10 | 0.1 | Negligible |
| | | 120 | 0.2 | |
| | | 1440 | 0.5 | |
| n-hexane | | 10 | 5.9 | 8.9 |
| | | 60 | 6.4 | 9.7 |
| | | 120 | 6.7 | 10.2 |
| p-xylene | 5.85 | 10 | 5.7 | 7.6 |
| | | 60 | 7.6 | 10.1 |
| | | 120 | 7.6 | 10.1 |
| m-xylene | 6.8 | 10 | 3.8 | 5.0 |
| | | 60 | 5.7 | 7.6 |
| | | 120 | 5.7 | 7.6 |
| cyclohexane | 6.0 | 10 | 3.2 | 4 |
| | | 60 | 3.5 | 4.4 |
| | | 120 | 3.9 | 4.9 |
| Symm tri-methyl benzene | 7.6 | 10 | 0.1 | Negligible |
| | | 1440 | 0.3 | |

*Lennard Jones Kinetic Diameter
See D W Breck "Zeolite Molecular Sieves" Wiley Interscience, 1974, p 636

The results demonstrate that zeolite EU-2 is extremely hydrophobic. Only a negligible fraction of the voidage available to hydrocarbons is available to water. The results with xylenes and cyclohexane suggest a port size near to 6A but with some pillar box type openings (10 ring window) which deny access of cyclohexane to about half of the voidage available to p-xylene.

The invention provides also a method of making zeolite EU-2 which comprises reacting an aqueous mixture comprising at least one oxide $XO_2$, at least one oxide $Y_2O_3$ and at least one alkylated derivative of a polymethylene α-ω diamine having the formula

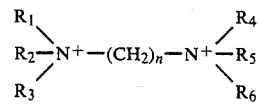

which by our definition is $Q^{2+}$ an amine degradation product thereof, or a precursor thereof, wherein n is in the range from 3 to 12, $R_1$ to $R_6$ which may be the same or different, can be alkyl or hydroxyalkyl groups containing from 1 to 8 carbon atoms and up to five of the groups $R_1$–$R_6$ can be hydrogen, the mixture having the molar composition:

| | |
|---|---|
| $XO_2/Y_2O_3$ | at least 70, preferably at least 150 |
| $OH^-/XO_2$ | 0.1 to 6.0 preferably 0.1 to 1.0 |
| $(M^+ + Q)/Y_2O_3$ | 0.5 to 100 |
| $Q/(M^+ + Q)$ | 0.1 to 1.0 |
| $H_2O/XO_2$ | 1 to 100 | where X is silicon and/or germanium, Y is one or more of aluminium, iron, gallium, boron, M is an alkali metal or ammonium and Q is the aforesaid alkylated derivative of a polymethylene diamine, an amine degradation product thereof, or a precursor thereof, of a related compound.

M and/or Q can be present as hydroxides or salts of inorganic or organic acids provided that $OH^-/XO_2$ requirement is fulfilled.

Preferred alkylated polymethylene diamine starting materials include alkylated hexamethylene diamines, especially methylated hexamethylene diamines, for example 1:6-N,N,N,N',N',N'-hexamethyl hexane-1,6-diammonium salts (e.g. halide, hydroxide, sulphate, silicate, aluminate).

Suitable precursors of the alkylated polymethylene diamine starting materials include the parent diamine along with alcohols or alkyl halides which can be used as such or can be preheated together in the reaction vessel preferably in solution (e.g. in methyl ethyl ketone) prior to addition of the other reactants required for zeolite EU-2 synthesis.

The preferred alkali metal (M) is sodium. The preferred oxide $XO_2$ is silica ($SiO_2$) and the preferred oxide $Y_2O_3$ is alumina ($Al_2O_3$).

The silica source can be any of those commonly considered for use in synthesising zeolites, for example powdered solid silica, silicic acid, colloidal silica or dissolved silica. Among the powdered silicas usable are precipitated silicas, especially those made by precipitation from an alkali metal silicate solution, such as the type known as "KS 300" made by AKZO, and similar products, aerosil silicas, fume silicas and silica gels suitably in grades for use in reinforcing pigments for rubber or silicone rubber. Colloidal silicas of various particle sizes may be used, for example 10–15 or 40–50 microns, as sold under the Registered Trade Marks "LUDOX" "NALCOAG" and "SYTON". The usable dissolved silicas include commercially available waterglass silicates containing 0.5 to 6.0, especially 2.0 to 4.0 mols of $SiO_2$ per mol of alkali metal oxide, "active" alkali metal silicates as defined in U.K. Pat. No. 1193254, and silicates made by dissolving silica in an alkali metal hydroxide or quaternary ammonium hydroxide or a mixture thereof.

The alumina source is most conveniently sodium aluminate, but can be aluminium, an aluminium salt, for example the chloride, nitrate or sulphate, an aluminium alkoxide or alumina itself, which should preferably be in a hydrated or hydratable form such as colloidal alumina, pseudoboehmite, boehmite, gamma alumina or the alpha or beta trihydrate.

The reaction mixture is usually reacted under autogenous pressure, optionally with added gas, e.g. nitrogen, at a temperature between 85° and 250° C. until crystals of zeolite EU-2 form, which can be from 1 hour to many months depending on the reactant composition and the operating temperature. Agitation is optional, but is preferable since it reduces the reaction time.

At the end of the reaction, the solid phase is collected on a filter and washed and is then ready for further steps such as drying, dehydration and ion-exchange.

If the product of the reaction contains alkali metal ions, these have to be at least partly removed in order to prepare the hydrogen form of EU-2 and this can be done by ion exchange with an acid, especially a strong mineral acid such as hydrochloric acid or by way of the ammonium compound, made by ion exchange with a solution of an ammonium salt such as ammonium chloride. Ion exchange can be carried out by slurrying once or several times with the ion-exchange solution. The zeolite is usually calcined after ion exchange but this may be effected before ion-exchange or during ion-exchange if the latter is carried out in a number of stages.

In general, the cation(s) of zeolite EU-2 can be replaced by any cation(s) of metals, and particularly those in Groups IA, IB, IIA, IIB, III (including rare earths) VIII (including noble metals) and by lead, tin and bismuth. (The Periodic Table is as in "Abridgements of Specifications" published by the UK Patent Office) Exchange is carried out using any water soluble salts containing the appropriate cation.

When used as a catalyst, zeolite EU-2 can be associated with an inorganic matrix, which can be either inert or catalytically active. The matrix may be present simply as a binding agent to hold the small zeolite particles (0.005 to 10 microns) together, or it may be added as a diluent to control the amount of conversion in a process which may otherwise proceed at too high a rate, leading to catalyst fouling as a result of excessive coke formation. Typical inorganic diluents include catalyst support materials such as alumina, silica, kaolinic clays, bentonites, montmorillonites, sepiolite, attapulgite, Fullers earth, synthetic porous materials such as $SiO_2$-$Al_2O_3$, $SiO_2$-$ZrO_2$, $SiO_2$-$ThO_2$, $SiO_2$-$BeO$, $SiO_2$-$TiO_2$ or any combination of these diluents. An effective way of mixing zeolite EU-2 with such diluents is to mix appropriate aqueous slurries in a mixing nozzle and then to spray-dry the slurry. Other ways of mixing can be used.

If zeolite EU-2 in any cationic form or as a catalytic composite is exchanged or impregnated with hydrogenation/dehydrogenation components, such as Ni, Co, Pt, Pd, Re, Rh, shape selective hydrocracking and reforming catalysts can be made, especially if the $Na_2O$ content is less than 0.1% w/w.

A wide range of shape selective hydrocarbon conversion catalysts can be prepared from zeolite EU-2 by ion exchange or impregnation with cations, or oxides, selected from the following, Cu, Ag, Mg, Ca, Sr, Zn, Cd, B, Al, Sn, Pb, V, P, Sb, Cr, Mo, W, Mn, Re, Fe, Co, Ni, noble metals.

Usually the Eu-2 catalyst will be in acid form, thus stoichiometry is maintained by $H^+$ or $H_3O^+$ as an additional balancing cation, or as sole cation. Such catalysts may find application in the following processes; hydrodesulphurization, hydrodenitrification, catalytic dewaxing, selective alkylation or alkanes, dehydration reactions and oxidation.

Methanol on dehydration by EU-2 or H-EU2 yields a wide range of aliphatic and aromatic hydrocarbons, demonstrating, high acidity and selectivity for propene, cis butene-2 and 2-methyl propane which is very surprising. H-EU2 may also be an effective aromatization catalyst.

Zeolite EU-2 may also find applications in the separation of aromatics and cycloparaffins, and in pollution control by its ability to remove organic contaminants from aqueous effluents as a result of its extreme hydrophobicity.

The invention is illustrated by the following Examples.

EXAMPLES 1-5

In these examples, the solid silica (CAB-O-SIL M5 $SiO_2/Al_2O_3$ ratio 3,400) was suspended in a mixture of hexamethonium bromide and water. Next a solution containing sodium hydroxide, and where appropriate sodium aluminate, was stirred in. The mixture was reacted in a stirred stainless steel autoclave under the reaction conditions indicated in Table 3.

TABLE 3

| Example | Reaction Mixture Composition | | | | | Temp °C. | Time (hrs) | Product |
|---|---|---|---|---|---|---|---|---|
| | $Na_2O$ | Q | $Al_2O_3$ | $SiO_2$ | $H_2O$ | | | |
| 1 | 567 | 567 | 1 | 3400 | 170,000 | 180 | 120 | EU-2 |
| 2 | 25 | 25 | 1 | 150 | 7,500 | 180 | 120 | EU-2 + trace EU-1* |
| 3 | 14.9 | 14.9 | 1 | 89.6 | 4,778 | 200 | 48 | EU-2 + trace EU-1* |
| 4 | 50 | 50 | 1 | 300 | 15,000 | 200 | 16 | EU-2 |
| 5 | 100 | 100 | 1 | 600 | 30,000 | 180 | 16 | EU-2 |

*Zeolite EU-1 is described in our copending UK Application No 8019210

EXAMPLE 6

Hydrogen EU-2 was prepared from the product of Example 5 as follows. First the product was dried overnight at 120° C. and then calcined for 48 hours in air at 450° C. The resulting sodium hydrogen EU-2 was used in the sorption work detailed in Table 2. A portion of this material was exchanged by slurrying for 1 hour at 25° C. with 5 ml NHCl per g of zeolite. The resulting hydrogen zeolite contained less than 500 ppm $Na_2O$

EXAMPLE 7

The catalytic activity of hydrogen EU-2 in the conversion of methanol to hydrocarbons was demonstrated in two pulse microreactors. Both were essentially the same except for the analysis systems, one of which determined $C_1-C_4$ hydrocarbons and the other of which determined $C_6$ (and above) hydrocarbons, particularly aromatics. A catalyst bed of about 0.3 ml of 3 mm pellets of hydrogen EU-2 was activated by calcination at 450° C. for 3 hours in a stream of nitrogen. With the catalyst temperature still at 450° C. a sample of methanol (0.6 μl) was injected above the catalyst bed. The $C_1-C_4$ hydrocarbon analysis is given in Table 4.

TABLE 4

| $C_1-C_4$ hydrocarbon analysis % v/v | |
|---|---|
| Methane | 1.7 |
| Ethane | 0.5 |
| Ethene | 8.8 |
| Propane | 7.5 |
| Propene | 17.8 |
| 2-methyl propane | 30.4 |
| Butane | 0.7 |
| Butene-1 | 1.9 |
| 2-methyl propene | 0 |
| trans-butene-2 | 2.9 |
| cis-butene-2 | 27.8 |

The high selectivities for propene, cis-butene-2 and 2-methylpropane are especially surprising.

Another sample of hydrogen EU-2 was activated in the same way and a 2 μl pulse of methanol was passed over the catalyst. The analysis of the aromatics formed is given in column A in Table 5. A second 2 μl pulse of methanol gave the results in column B. Two 10 μl pulses of methanol were separately passed over the catalyst bed, followed by a further single pulse of 2 μl. The results are given in column C. Six 10 μl pulses of methanol were separately passed over the catalyst, followed again by a further single pulse of 2 μl. The results are given in column D.

TABLE 5

| | Aromatics analysis (% v/v) | | | |
|---|---|---|---|---|
| | A | B | C | D |
| Benzene | 7.9 | 7.0 | 6.8 | 4.6 |
| Toluene | 26.8 | 26.3 | 27.9 | 28.9 |
| Ethylbenzene | 35.1 | 34.7 | 32.7 | 35.3 |
| + m,p-xylene) | | | | |
| o-xylene | 6.7 | 6.9 | 8.1 | 6.5 |
| $C_9$ aromatics | 9.6 | 9.8 | 10.5 | 10.8 |
| $C_{10+}$ aromatics | 14.0 | 15.3 | 13.9 | 13.8 |

Some $C_5$ and $C_6$ aliphatic hydrocarbons were also formed. The total yield of hydrocarbons did not change perceptibly with ageing.

What we claim is:

1. A method of making zeolite EU-2 having a molar composition expressed by the formula:

0.5 to $1.5R_2O:Y_2O_3$:at least $70XO_2$:0 to $100H_2O$ wherein R is a monovalent cation or 1/n of a cation of valency n, X is silicon and/or germanium, Y is one or more of aluminum, iron, gallium or boron, and $H_2O$ is water of hydration additional to water notionally present when R is H, and having an X-ray diffraction pattern substantially as set out in Table 1, which method comprises reacting an aqueous mixture comprising at least one oxide $XO_2$, at least one oxide $Y_2O_3$ and at least one alkylated derivative of a polymethylene α–ω diamine having the formula:

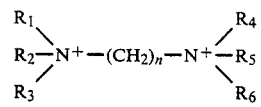

wherein n is in the range from 3 to 12, $R_1$ to $R_6$ are each methyl, the mixture having the molar composition:

| $XO_2/Y_2O_3$ | at least 70 |
|---|---|
| $OH^-/XO_2$ | 0.1 to 6.0 |
| $(M^+ + Q)/Y_2O_3$ | 0.5 to 100 |
| $Q/(M^+ + Q)$ | 0.1 to 1.0 |
| $H_2O/XO_2$ | 1 to 100 | where X is silicon and/or germanium, Y is one or more of aluminum, iron, gallium, boron, M is an alkali metal or ammonium and Q is the aforesaid alkylated derivative of a polymethylene diamine, or a precursor thereof.

2. A method according to claim 1 wherein the $XO_2/Y_2O_3$ molar ratio is at least 150.

3. A method according to claim 1 or claim 2 wherein the $OH^-/XO_2$ ratio is in the range 0.1 to 1.0.

4. A method according to claim 1 wherein the alkylated hexamethylene diamine is an $N,N,N,N^1,N^1,N^1$-hexamethyl-1,6-hexamethylene diammonium salt.

* * * * *

UNITED STATES PATENT AND TRADEMARK OFFICE
CERTIFICATE OF CORRECTION

PATENT NO. : 4,741,891

DATED : May 3, 1988

INVENTOR(S) : CASCI et al.

It is certified that error appears in the above-identified patent and that said Letters Patent is hereby corrected as shown below:

On the face of the patent, change "[75] Inventors: John L. Casci, Redcar, England; Barrie M. Lowe, Edinburgh, Scotland; Thomas V. Lowe, Darlington, England" to --[75] Inventors: John L. Casci, Redcar, England; Barrie M. Lowe, Edinburgh, Scotland; Thomas V. Whittam, Darlington, England--.

Signed and Sealed this

Fifth Day of November, 1991

*Attest:*

HARRY F. MANBECK, JR.

*Attesting Officer*   *Commissioner of Patents and Trademarks*